United States Patent
Atkinson

(10) Patent No.: US 9,488,633 B2
(45) Date of Patent: Nov. 8, 2016

(54) METHOD FOR DETERMINING THE CONCENTRATION OF IRON IONS IN HYDROCARBON COMPOSITIONS

(71) Applicant: Parker-Hannifin Corporation, Cleveland, OH (US)

(72) Inventor: David Atkinson, Littlehampton (GB)

(73) Assignee: Kittiwake Developments Ltd., Hempel Hempstead, Herfordshire (GB)

( * ) Notice: Subject to any disclaimer, the term of this patent is extended or adjusted under 35 U.S.C. 154(b) by 226 days.

(21) Appl. No.: 14/301,446

(22) Filed: Jun. 11, 2014

(65) Prior Publication Data

US 2015/0160179 A1 Jun. 11, 2015

(30) Foreign Application Priority Data

Dec. 5, 2013 (EP) .................................... 13195943

(51) Int. Cl.
*G01N 33/22* (2006.01)
*G01N 21/78* (2006.01)
(Continued)

(52) U.S. Cl.
CPC .............. *G01N 33/22* (2013.01); *G01N 31/22* (2013.01); *G01N 21/78* (2013.01); *G01N 33/28* (2013.01); *G01N 33/2835* (2013.01); *G01N 33/2858* (2013.01); *G01N 33/2888* (2013.01); *Y10T 436/21* (2015.01)

(58) Field of Classification Search
CPC ...... G01N 21/78; G01N 31/22; G01N 33/20; G01N 33/22; G01N 33/26; G01N 33/28; G01N 33/2835; G01N 33/2888; Y10T 436/18; Y10T 436/182; Y10T 436/20; Y10T 436/201666; Y10T 436/21; Y10T 436/212; Y10T 436/214; Y10T 436/216

USPC ............ 436/60, 73, 84, 119, 120, 127, 129, 436/139–142, 164, 166, 171; 422/82.09, 422/68.1
See application file for complete search history.

(56) References Cited

U.S. PATENT DOCUMENTS

| | | | | |
|---|---|---|---|---|
| 3,506,403 A | * | 4/1970 | Senkowski | G01N 31/22 436/84 |
| 3,667,915 A | * | 6/1972 | Klein | G01N 33/84 436/53 |
| 3,709,662 A | | 1/1973 | Hach | |

(Continued)

FOREIGN PATENT DOCUMENTS

| | | |
|---|---|---|
| CN | 101975688 | 12/2011 |
| EP | 0469773 | 2/1992 |

(Continued)

OTHER PUBLICATIONS

ASTM Standard E1615, "Standard Test Method for Iron in Trace Quantities Using for FerroZine Method", ASTM International, West Conshohocken, PA, DOI: 10.1520/D1615-08, 2008.

(Continued)

*Primary Examiner* — Maureen Wallenhorst
(74) *Attorney, Agent, or Firm* — Christopher Hunter

(57) ABSTRACT

The present invention relates to a method for determining the concentration of iron ions in a hydrocarbon composition, as well as reagents and kits for use in such methods. The method utilises a thiocarboxylic acid having formula (I) which reduces the ferric ions and complexes ferrous ions producing a colored solution, which can be analysed to determine the amount of iron ions in the starting sample.

14 Claims, 1 Drawing Sheet

(51) Int. Cl.
*G01N 31/22* (2006.01)
*G01N 33/28* (2006.01)

(56) References Cited

U.S. PATENT DOCUMENTS

| | | | |
|---|---|---|---|
| 3,834,821 A * | 9/1974 | Ferrari ................ | G01N 21/255 356/246 |
| 4,203,725 A | 5/1980 | Snowden, Jr. | |
| 4,238,197 A | 12/1980 | Eisentraut | |
| 4,324,758 A | 4/1982 | Eisentraut | |
| 6,491,824 B1 | 12/2002 | Lin | |
| 8,003,581 B1 | 8/2011 | Vinson | |
| 2006/0270050 A1 | 11/2006 | Naudts | |
| 2009/0227035 A1 | 9/2009 | Naudts | |
| 2012/0142113 A1 | 6/2012 | Banks | |
| 2012/0309097 A1 | 12/2012 | Boudenne | |

FOREIGN PATENT DOCUMENTS

| | | |
|---|---|---|
| WO | 2009/077557 | 6/2009 |
| WO | 2010/107893 | 9/2010 |
| WO | 2012/061590 | 5/2012 |
| WO | 2013/090138 | 6/2013 |

OTHER PUBLICATIONS

Bernhardt, H. et al., "The Continuous Determination of Low Level Iron, Soluble Phosphate, and Total Phosphate with the AutoAnalyzer," *Technicon Symposium*, "Automation in Analytical Chemistry", Oct. 3, 1967.

Davenport Jr., W. H. et al., Ammonium Thioglycolate as a Colorimetric Analytical Reagent for Uranium (VI) in the Presence of Various Anions, Oak Ridge National Laboratory, 1948.

Leussing, D. L. et al., "Iron-Thioglycolate Complexes", *Journal of the American Chemical Society*, 25, 6, Aug. 1, 1953.

Lyons, Edward, Thiogylcolic Acid as a Color Test for Iron, *J. Am. Chem. Soc.*, 49, 1916, Aug. 5, 1927.

Man Diesel and Turbo, Service letter SL2013-571/JAP, 2013.

McConnell, G. et al., A Wear Theory for Low Speed Diesel Engines Burning Residual Fuel, *Wear*, 5, 43-54, 1962.

Miyake, Shinichi et al., "Cylinder Lining and Piston Ring Lubrication Issues in Relation to Increase Stroke/Bore Ration," *CIMAC* Congress Paper 177, 2013.

Naegeli, D. W. et al, "Role of Sulfur Oxides in Wear and Deposit Formation in Army Diesel Engines," Interim Report BFLRF No. 248, Dec. 1988.

Partial European Search Report for EP Patent Application 13195943.9, Apr. 10, 2014.

Seeling, A. et al., "Photometric Determination of Iron Contamination of Drugs and Biological Matrices," *Pharmazie*, 58(5), 312-314 (English abstract), May 2003.

Swank, H. W. et al., The Determination of Iron with Mercaptoacetic Acid, *Ind. Eng. Chem. Anal.* Ed., 10, 7, 1938.

Tischler, A., "Determination of Iron Contamination of Used Lubricating Oil for Use in Measuring Rates of Wear in Aircraft Engines," *National Advisory Committee for Aeronautics*, Restricted Bulletin 4C25, Mar. 1944.

Van Helden, A. K. et al, "Corrosive Wear in Crosshead Diesel Engines," *Tribol. Int.*, 22, 189, 1989.

Verbeeke, Luc et al., "Reliable Lubrication of Low Speed Engines Operated with Varying Fuel Sulphur Levels," *CIMAC* Congress, Paper 120, 2013.

* cited by examiner

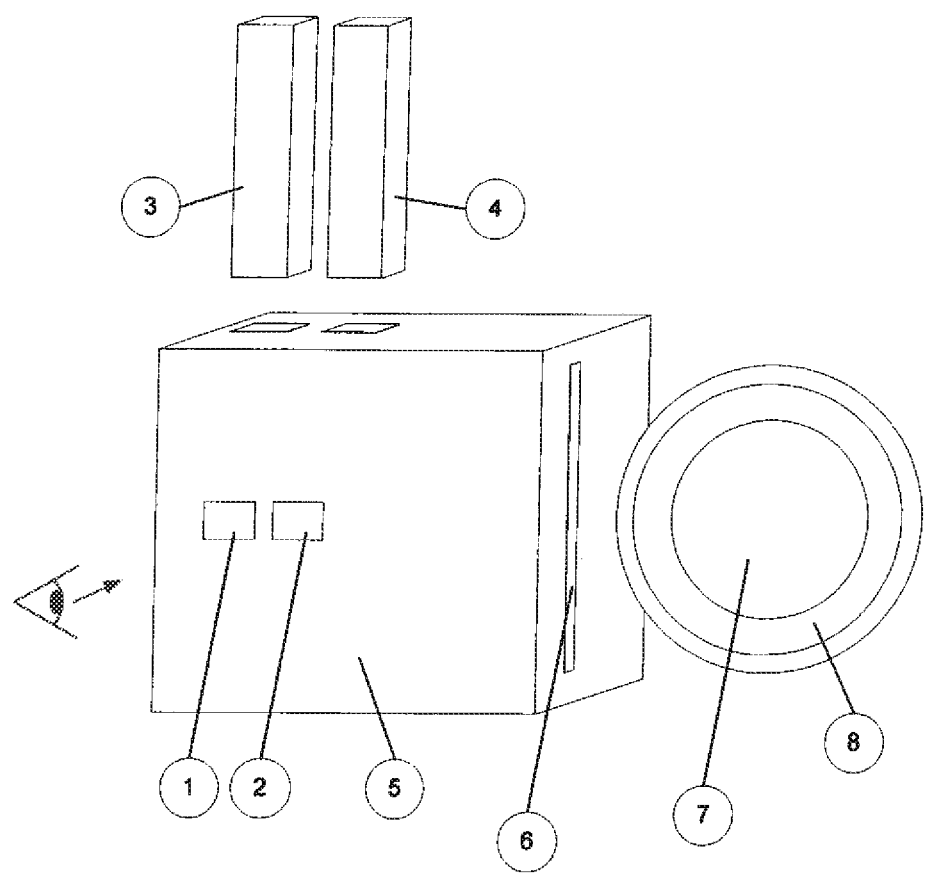

METHOD FOR DETERMINING THE CONCENTRATION OF IRON IONS IN HYDROCARBON COMPOSITIONS

CROSS-REFERENCE TO RELATED APPLICATIONS

This application claims priority to European Patent Application No. 13195943.9 entitled "Method for Determining the Concentration of Iron Ions in Hydrocarbon Compositions," filed on 5 Dec. 2013; the disclosure of which is incorporated herein by reference in its entirety.

FIELD OF THE INVENTION

The invention relates to methods for determining the concentration of iron ions in a hydrocarbon composition, as well as reagents and kits for use in such methods. The invention particularly relates to methods of determining the concentration of iron ions in oil such as cylinder oil from marine engines.

BACKGROUND

Iron may be present in hydrocarbon mixtures due to corrosion of the vessels which contain the hydrocarbon. The detection of iron in hydrocarbon mixtures is therefore desirable, as it can act as an indicator of corrosion. However, many of the methods which are known in the art are either inadequate or time consuming.

One area where the detection of iron levels is particularly important is in cylinder oil for combustion engines, particularly marine engines which can be run at lower temperatures. The internal components of engines, particularly the cylinder lining of combustion engines, are subject to degradation due to a combination of corrosion, adhesive and abrasive wear. Under normal operating conditions, corrosive wear contributes most of the total wear of a machine or engine lining.

This corrosion is caused by chemical reactions between the piston rings and/or cylinder lining and acidic products associated with the combustion of sulphur-rich oils.

If the engine temperature is below the dew point of sulphuric acid, the acid can build up on the cylinder liners thereby promoting their "cold corrosion".

The problem of cold corrosion can be exacerbated by engine and machine operators trying to conserve fuel. For example, more recently ship operators have taken to running diesel engines at reduced speeds (so-called slow steaming) as a means of improving fuel consumption. However, this reduction in speed causes the engine temperature to drop, increasing the levels of sulphuric acid in the oil and accelerating the cold corrosion process.

Corrosion of the piston rings and/or lining of a cylinder in a machine or engine can decrease the efficiency of the machine or engine, and will also result in a build-up of contaminant in the oil or hydrocarbon used for lubricating the cylinders. At its extreme, corrosion reduces efficiency and eventually can damage an engine to such an extent that it can no longer be used. It is therefore desirable to provide methods which are capable of detecting corrosion and particularly cold corrosion at an early stage, so that preemptive measures can be used to mitigate further damage.

Corrosion of a machine or engine can be reduced by, for example, increasing the flow of lubricant. However, lubricant can be expensive, and replacing it unnecessarily will often incur significant costs.

It has become standard practice onboard large marine vessels to monitor the used engine lubricant for contaminants, in particular iron, with a view to determining the wear rate of the engine.

The iron found in used cylinder lubricant typically exists in one of three oxidation states, each one having its own particular properties. For example, metallic iron particles worn off the cylinder liner have an oxidation state of 0, which exhibits strong ferromagnetism. In addition to the metallic particles worn off a machine or engine, other corrosion products are found. For example, iron sulphate is a likely product of the reaction between sulphuric acid and the lining of a machine or engine. In contrast to metallic iron, the iron in iron sulphate has an oxidation state of +2, and hence cannot be detected magnetically. The same is true of other corrosion products such as rust, where iron has an oxidation state of +3.

It is possible to detect wear that produces metallic iron particles using a magnetometer, such as the Parker Kittiwake LinerSCAN. However, by the time that magnetometry registers the presence of metallic iron particles, significant damage to the machine or engine may have already occurred.

Previously methods for determining the levels of iron contaminant in used lubricant have involved sending samples of the oil to laboratories relatively far removed from the operational site. However, this process took a long time, during which critical damage to the machine or engine could occur.

Methods are now available that use an on-site method for determining the concentration of iron contaminants, allowing the current corrosion status of the engine to be determined more quickly.

For example, the MobilGard Monitor by ExxonMobil is a portable oil tester that uses the distortion of the magnetic flux field to determine the amount of iron in the 0 oxidation state.

U.S. Pat. No. 4,203,725 relates to an on-site method for determining the need for replacement of oil due to the build-up of metallic contaminant material therein, involving vigorously mixing a known volume of oil in a known volume of aqueous solvent, including a reagent capable of reacting with the metal and/or metal oxide, and comparing the color as generated to a standard color to determine the concentration of the metal contaminant. However, this method takes several hours to test for the concentration of iron in the used oil.

U.S. Pat. No. 4,238,197 relates to a method for analyzing used lubricating oil for iron wear metal content, in which all of the iron in a sample of the oil is extracted into an oil immiscible layer. Buffering and reducing agents are added, and the iron in the solution is reacted with a chelating agent to form a red complex indicative of the iron content. However, this is again a slow process, and uses separate reducing and chelating agents.

The Chevron DOT.FAST drip oil analyser analyses the iron concentration of an oil sample. It uses a solvent to reduce any iron (III) in the oil sample to iron (II) and quantifies the iron (II) content colorimetrically. However, it also uses separate reducing and complexing agents, and measures the total iron content of an oil sample, not just the ferrous and ferric content. It also requires a filtration step, which means the process can take many hours to complete.

Hence whilst there are methods for determining corrosion (particularly cold corrosion) by measuring the iron content of oils, these methods are relatively slow. The present invention seeks to provide fast, effective and simple methods for detecting ferrous and ferric ions in hydrocarbon mixtures. The present invention also seeks to provide methods of detecting the early signs of cold corrosion before any significant damage has been done to the machine or engine.

SUMMARY OF THE INVENTION

The present invention provides a method for determining the concentration of iron ions in a hydrocarbon composition, said method comprising:
a) providing a hydrocarbon composition;
b) reacting the hydrocarbon composition with a reagent composition and optionally a diluent composition comprising a non-polar solvent to provide a test sample, characterized in that
the reagent composition comprises water and a compound according to formula (I):

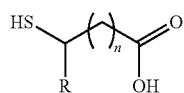

wherein
n denotes an integer from 0 to 3, and
R denotes H, alkyl or aryl, and
wherein the reagent composition has a pH of 7.5 or above; and
c) determining the concentration of iron ions in the hydrocarbon sample by determining the amount of complex formed between the compound of formula (I) and iron ions in the test sample.

The invention further provides a kit comprising:
a) a diluent composition comprising a non-polar solvent; and
b) a reagent composition comprising water and a compound according to formula (I):

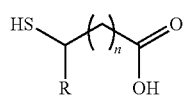

wherein
n denotes an integer from 0 to 3, and
R denotes H, alkyl or aryl, and
wherein the reagent composition has a pH of 7.5 or above.

The invention also provides the use of the above kit to detect corrosion, preferably corrosion in an engine, particularly preferably cold corrosion in a marine engine.

The method of the invention involves the preparation of a test sample from a reagent composition and the hydrocarbon composition. The reagent composition contains water, and it will therefore typically be immiscible with the hydrocarbon composition which is being tested. The test sample will therefore typically phase separate to form an aqueous phase and a hydrocarbon phase.

The ferrous ions present in the hydrocarbon composition will typically be soluble in water, and will therefore readily transfer to the aqueous phase on formation of the test sample. The ferric ions typically have low water solubility. However, the compounds of formula (I) reduces the ferric ions to ferrous ions, promoting their solubility in the aqueous phase.

The compound of formula (I) serves a dual purpose, since it also complexes to ferrous ions in an aqueous phase to form a colored complex. Step c) of the method of the invention involves analysing the test sample to determine the amount of complex which is formed between the ferrous ions and the compound of formula (I).

The hydrocarbon composition being analysed may be highly viscous, as is often the case with used engine oils. The method of the invention therefore preferably uses a diluent composition to dilute the hydrocarbon composition, reducing its viscosity and facilitating better mixing with the reagent composition. The diluent also ensures that smaller amounts of the hydrocarbon composition are used, ensuring the properties of the test sample (miscibility of components, relative solubility of the complexed iron etc.) are largely independent of the hydrocarbon composition which is being tested. The diluent composition contains a non-polar solvent.

The various aspects and preferred embodiments of the invention will be described in more detail below.

LIST OF FIGURES

FIG. 1—Schematic of a hand held apparatus suitable for carrying out the method of the invention.

DETAILED DESCRIPTION OF THE INVENTION

The present invention provides a method for determining the amount of iron ions (i.e. ferrous and ferric ions) in a hydrocarbon composition, and a reagent and kit for use in the same. The method is selective at detecting ferrous and ferric ions, and does not detect particles of metallic iron (i.e. iron in an oxidation state of 0 present as metal particles).

The method of the invention can include an additional step of detecting the amount of metallic iron in the hydrocarbon composition, such as by using magnetometry.

The method of the invention is particularly effective at determining the corrosion state of a combustion engine by detecting early indicators of cold corrosion. The invention therefore lies in part in the recognition that ferrous and ferric ions become present in engine oils, particularly cylinder oils, as contaminants due to cold corrosion, before iron metal particles.

The present invention therefore provides a method for detecting the early signs of cold corrosion in a combustion engine, and reagents and kits for use in such methods.

By "ferrous iron" is meant $Fe^{2+}$, namely iron in an oxidation state of +2.

By "ferric iron" is meant $Fe^{3+}$, namely iron in an oxidation state of +3.

The various compositions and steps which are involved in the method will now be described in more detail.

The hydrocarbon composition may in principal be any hydrocarbon that contains (or may contain) ferrous and/or ferric ions. For example, the hydrocarbon composition could be a liquid fraction from a refinery process which contains ferrous and/or ferric ions as contaminants due to corrosion of the refinery equipment.

By "refinery process" is meant a process in which hydrocarbons are separated using fractional distillation and/or converted using heat in processes such as thermal cracking.

As noted above, the method of the invention finds particular use for detecting cold corrosion of combustion engines, particularly combustion engines on marine vessels.

The hydrocarbon composition may therefore be an engine oil, preferably a cylinder oil. Preferably, the hydrocarbon composition is a spent engine oil, preferably a spent cylinder oil.

By "marine vessels" is meant ships and boats. A "marine engine" is therefore a combustion engine on a ship or boat.

By "engine oil" is meant an oil or lubricant for a combustion engine.

By "cylinder oil" is meant an oil or lubricant for cylinders of combustion engines.

By "spent" is meant an oil or lubricant which has been used. A "spent engine oil" is therefore an engine oil which has been used in a combustion engine.

Typically, combustion engines in marine vessels are very large. A typical cylinder may be several cubic meters in volume. Cylinder oil is continually or intermittently fed to ensure adequate lubrication during operation. These engines will therefore have a drain which continually removes the spent oil, allowing it to be sampled for use in the method of the invention.

Other situations where the method of the invention finds particular use is in testing spent cooking oil, particularly in industrial scale food production lines. Thus, the equipment in such lines is typically made from stainless steel, and the presence of ferrous and ferric ions can provide an early warning of corrosion of internal components in the processing equipment which are not readily available for inspection.

In a similar manner, the method of the invention can also be used to test for the presence of ferrous and ferric ions in edible oils such as palm oil, olive oil, sunflower oil, rapeseed oil, groundnut oil or the like. Typically, the iron content of such oils is very low, with many edible oils having nominally zero iron content (palm oil and sunflower oil, for example). If ferrous or ferric ions are present, or present at levels higher than expected, this can provide an early warning of corrosion in the processing equipment.

In many applications, the diluent composition is not needed, as it is perfectly possible to mix the hydrocarbon composition with the reagent composition to allow transfer of the ferrous/ferric ions into the aqueous phase. However, this can lead to inaccuracies in the method if the iron complex is partly soluble in the hydrocarbon composition, which will lead to lower levels of the iron complex being present in the aqueous phase. Moreover, solvatochromic effects may mean that the absorption properties of the iron complex differ if the hydrocarbon is partly or fully miscible in water. Both these effects may lead to inaccuracies in the final result.

In order to mitigate these issues, it is preferred to use small amount of hydrocarbon composition in combination with a diluent composition, such that the test sample contains mainly reagent composition and diluent composition. The properties of the resultant test will remain largely unaffected by the hydrocarbon composition which is being tested.

The optional diluent composition finds particular use when the hydrocarbon composition is particularly viscous, such as is the case with spent engine oils. These types of oils may be so viscous that they are physically incapable of mixing with the aqueous reagent composition in a reasonable timescale and without significant input of energy (such as by agitation or sonication).

The diluent composition comprises a non-polar solvent, the primary function of which is to provide the non-aqueous phase which phase separates in the test sample. The non-polar solvent also reduces the viscosity of the hydrocarbon composition rendering it capable of being mixed with the reagent composition.

The diluent composition may be combined with the hydrocarbon composition prior to mixing with the reagent composition to form the test sample. Alternatively, the diluent composition can be added to the test sample itself. Alternatively, the diluent composition, reagent composition and hydrocarbon composition can be combined simultaneously to form the test sample.

By "non-polar solvent" is meant a solvent with a low dielectric constant, preferably with a dielectric constant below 5.

As used herein, the dielectric constant is measured at 25° C., for example using a BI-870 from Brookhaven Instruments.

Preferred non-polar solvents are selected from aliphatic hydrocarbons, aromatic hydrocarbons and ethers, with aliphatic hydrocarbons, aromatic hydrocarbons and mixtures thereof being particularly preferred.

The non-polar solvent preferably has relatively low volatility and low viscosity. Therefore, highly volatile aliphatic hydrocarbons such as pentane and low boiling petroleum ethers are less preferred. Thus, while such solvents work perfectly well, on a practical level they are less favourable to work with due to the fumes which inevitably arise.

Preferred non-polar solvents are petroleum distillates, such as mineral spirits, kerosene, naphtha, and heavy distillate (CAS #64741-65-7), with naphtha and heavy distillate being particularly preferred.

The reagent composition comprises water and is typically aqueous (i.e. water constitutes at least 50% by volume of all of the liquid in the reagent composition). The reagent composition additionally comprises a compound of formula (I):

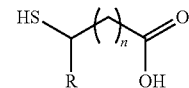

wherein
n denotes an integer from 0 to 3, and
R denotes H, alkyl or aryl.
Preferably, n denotes 0 or 1, most preferably n denotes 0.
Preferably, R denotes H, $C_1$-$C_6$ alkyl or $C_6$-$C_{10}$ aryl.
More preferably, R denotes H or $C_1$-$C_6$ alkyl, even more preferably, R denotes H or $C_1$-$C_4$ alkyl, even more preferably R denotes H, methyl or ethyl.
Most preferably, R denotes H or methyl, with H being the most preferred.
Thus, particularly preferred are compounds of formula (I) in which
n denotes 0; and
R denotes H, methyl or ethyl.
Thus, especially preferred are compounds of formula (I) in which
n denotes 0; and
R denotes H or methyl.
The most preferred compound of formula (I) is thioglycolic acid.

Although other thiocarboxylic acids may be capable of complexing with iron, the present invention uses compounds of formula (I) due to the balance of relative solubilities in the aqueous and non-aqueous phases of the test sample. If the complexed iron is too soluble in the non-aqueous phase, at least some of the ion complex will remain in this phase which reduces the accuracy of the method of the invention.

As used herein, "alkyl" is intended to include both branched and straight-chain saturated aliphatic hydrocarbon groups containing, if specified, the specified number of carbon atoms. For example, "$C_1$-$C_6$ alkyl" is intended to include $C_1$, $C_2$, $C_3$, $C_4$, $C_5$ and $C_6$ alkyl groups. Examples of alkyl include, but are not limited to, methyl, ethyl, n-propyl, i-propyl, n-butyl, i-butyl, sec-butyl, t-butyl, n-pentyl, n-hexyl, 2-methylbutyl, 2-methylpentyl, 2-ethylbutyl, 3-methylpentyl, and 4-methylpentyl.

As used herein, the term "aryl", is intended to mean an aromatic moiety containing, if specified, the specified number of carbon atoms; for example phenyl or naphthyl.

The reagent composition has a pH of 7.5 or above. At these high pH levels, the carboxylic acid group in the compound of formula (I) is in its deprotonated form when present in the reagent composition. Thus, although herein it is specified that the reagent composition contains a compound of formula (I) having the structure shown above, the skilled person would recognise that this compound is typically present in the reagent composition in the following form:

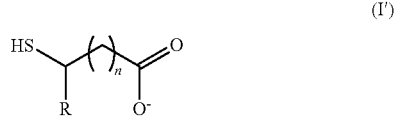

(I')

wherein the compound is accompanied by an appropriate cation. For the avoidance of doubt, any reference to the compound of formula (I) herein should be understood to also be a reference to a compound of formula (I'). Thus, the reagent composition can be formed by combining water and a compound of formula (I) (e.g. thioglycolic acid), and then adjusting the pH to 7.5 or above (thus inevitably forming a compound of formula (I')), or alternatively combining a compound of formula (I') (e.g. ammonium thioglycolate) and water, and adjusting the pH to 7.5 or above (if necessary).

Thus, preferably the reagent composition contains a compound of formula (I), or an ammonium, alkali metal or alkaline earth metal salt thereof.

The reagent composition has a high pH to ensure the compound of formula (I) is capable of acting as a reducing and complexing agent. This simultaneously has the advantage that the reagent composition does not solubilise any metallic iron particles which may be present. Moreover, if the pH of the aqueous phase of the test sample is too low, it can inhibit the ability of the compound of formula (I) to reduce the ferric ions and complex with the ferrous ions.

However, at very high pH values (>12), the thiol itself can become deprotonated, causing subtle color changes in the complex.

The pH of the reagent composition is therefore preferably from 7.5 to 13, more preferably from 8 to 12, more preferably from 8.5 to 11, most preferably from 9 to 10.

Other preferred pH ranges for the reagent composition include from 8 to 11, most preferably from 9 to 11.

The relevant pH is not necessarily the reagent composition; it is actually the aqueous phase of the test sample which should remain in this range. Although the reagent composition effectively forms the aqueous phase of the test sample, the hydrocarbon composition can affect the pH of this phase.

For example, if the hydrocarbon composition contains acidic components, it may lower the pH to render the compound of formula (I) ineffective.

To mitigate this issue, the reagent composition preferably contains a buffer.

By "buffer" is meant a mixture of a mixture of a weak acid and its conjugate base or a weak base and its conjugate acid which ensure the pH of the composition changes by relatively small amounts on addition of further acids or bases. The concept of buffers is well known in the art, and the skilled person would have no difficulties formulating a suitable buffer to control the pH within a given range.

Preferably, the reagent composition contains a buffer to control the pH in a range of from 7.5 to 13, preferably from 8 to 12, more preferably from 8 to 11, more preferably from 8.5 to 11, preferably from 9 to 11, and most preferably from 9 to 10.

Examples of suitable agents that could be used in the buffer system include, but are not limited to, ADA (i.e. N-(2-acetamido)iminodiacetic acid), PIPES (i.e. piperazine-N,N'-bis(2-ethanesulfonic acid), ACES (i.e. N-(2-acetamido)-2-aminoethanesulfonic acid), BES (i.e. ($HOCH_2CH_2$)$_2$—$NCH_2CH_2SO_3H$), MOPS (i.e. 3-(N-morpholino)propanesulfonic acid), phosphate, TES (i.e. 2-[[1,3-dihydroxy-2-(hydroxymethyl)propan-2-yl]amino]ethanesulfonic acid), HEPES (i.e. 2-[4-(2-hydroxyethyl)piperazin-1-yl]ethanesulfonic acid), Tris (or THAM, i.e. tris (hydroxymethyl)aminomethane), tricine (i.e. N-(2-hydroxy-1,1-bis(hydroxymethyl)ethyl)glycine), bicine (i.e. 2-(bis(2-hydroxyethyl)amino)acetic acid), TAPS (i.e. 3-[[1,3-dihydroxy-2-(hydroxymethyl)propan-2-yl]amino]propane-1-sulfonic acid), ethanolamine, CHES (i.e. 2-(cyclohexylamino)ethanesulfonic acid), CAPS (i.e. 3-(cyclohexylamino)-1-propanesulfonic acid), methylamine, and piperidine. Using any of these agents, the pH of the buffer can be adjusted away from the $pK_a$ of the starting material by up to ±1 units using either a strong monobasic or monoprotic acid, such as sodium hydroxide or hydrochloric acid.

Particularly preferred agents for use in the buffer composition include amines such as ethanolamine.

Preferably, the buffer composition additionally contains ammonia.

The hydrocarbon composition is typically immiscible with the reagent composition. The test sample therefore typically phase separates to form an aqueous phase and a hydrocarbon phase. However, the amount of phase separation and particularly the relative solubility of the iron complex between the aqueous phase and hydrocarbon phase can vary. It is therefore preferred to use a diluent composition in order to ensure that there is phase separation in the test sample, and that the iron complex resides in the aqueous phase after phase separation.

Step b) of the method of the invention involves "reacting" the hydrocarbon composition with the reagent composition to form a test sample. By "reacting" is meant that the reagent and hydrocarbon compositions are allowed to mix to allow transfer of the iron ions from the non-polar phase to the aqueous phase of the reagent composition. Thereafter, the compound of formula (I) reduces the ferric ions to ferrous ions, and complexes to any ferrous ions which may be present.

No further external reagents are required to ensure that the reaction takes place, other than some modest input of mechanical energy to ensure that the aqueous and non-aqueous phases of the test sample actually mix. Upon mixing, the phase transfer, reduction and complexing steps will inevitably take place, given enough time.

The method of the invention will thus typically involve agitating the test sample to ensure thorough mixing of the aqueous and hydrocarbon phase, then allowing the test sample to phase separate. The agitation may be by any suitable means, such as by shaking the sample (e.g. by hand or on a shaking table) or stirring (e.g. using a stirrer bean or paddle).

In order to ensure efficient phase separation, the reagent composition preferably contains a salt to increase its ionic strength. Thus, the salt is highly lipophobic and will exert a strong preference to reside in the aqueous phase. The higher the ionic strength of the reagent composition, the greater the tendency for the aqueous phase to separate from the hydrocarbon phase and maximise energy of solvation of the salt(s).

Preferred salts are selected from metal halides, metal sulphates and metal nitrates, with metal halides being preferred. Particularly preferred salts are alkali and alkaline earth metal halides (preferably chlorides), such as sodium chloride and/or potassium chloride.

During the mixing and agitation step (step b)), the ferrous and ferric ions are transferred from the hydrocarbon phase to the aqueous phase. In order to facilitate this transfer, it is preferred to add a phase transfer agent that is miscible or soluble in both the aqueous phase and the hydrocarbon phase, and which is capable of interacting with the ferrous and ferric ions to aid in their movement between the two phases.

Typically, the phase transfer agent is a polar solvent, with alcohols being particularly preferred. Preferred phase transfer agents are selected from methanol, ethanol, n-propanol, i-propanol, butanol, pentanol, and hexanol, with methanol, ethanol, n-propanol, i-propanol and butanol being more preferred and i-propanol being particularly preferred.

The phase transfer agent may be present in the diluent composition, the reagent composition, or it may be added separately when combining the various compositions to form the test sample. However, the presence of salt in the reagent composition typically reduces the miscibility of the phase transfer agent in water, and therefore it is preferable to include the phase transfer agent in the diluent composition.

In the method of the invention, the ferric and ferrous ions in the hydrocarbon composition are transferred to the aqueous phase of the test sample and the ferric ions are reduced to yield ferrous ions which complex with the compound of formula (I). The complex is highly colored, and it is the presence of this color that can be detected in the analysis step to determine the concentration of ferrous and ferric ions that were present in the hydrocarbon composition.

The analysis step may involve detecting the complexed ferrous ions using colorimetry or UV-Vis spectroscopy. However, the method of the invention has distinct advantages over other methods due to its speed and simplicity, allowing it to be carried out without the need for complex lab equipment and laborious analytical techniques. Consequently, the analysis step preferably involves comparing the color of the aqueous phase of the test sample with a color chart.

By "color chart" is meant a graded chart of various intensities of a color which correspond to approximate concentrations of the total amount of ferrous and ferric ions in the aqueous phase of the test sample.

The color chart is a relatively crude means to evaluate the ion concentrations, giving only approximate results. However, its simplicity is advantageous, since it allows a rapid evaluation of the concentration using only simple apparatus. For example, the test sample may be prepared in a vial, shaken to ensure proper mixing, allowed to phase separate and then held up against a color chart.

The color chart used in the method of the invention will be predetermined depending on the compound of formula (I) (the different complexes of these compounds absorb light at different wavelengths), and the concentration of iron which is being detected. A typical color chart might be banded to detect iron at levels of 0-20 ppm, 20-40 ppm, 40-60 ppm etc., for example. Typically, the ferrous and ferric ion concentration of the hydrocarbon composition is not known. Consequently, a small sample of the hydrocarbon composition can be used initially (diluted if necessary), and if no observable color is seen progressively larger amounts of the hydrocarbon composition can be tested until the amount of ferrous-complex formed provides a meaningful value on the color chart which is being used. An alternative approach would be to start with a large hydrocarbon sample, and if the result returned is the maximum on the color chart, progressively smaller amounts of hydrocarbon composition may be used until a meaningful reading is obtained.

In some circumstances, the hydrocarbon composition itself can be colored, and some of the colored components may transfer into the aqueous phase along with the iron ions. While this may not be too problematic if spectroscopic means are being used to detect the ferrous complex, it may have an impact on how the results are compared to the color chart. To take account of this, it is preferred to use a blank composition to prepare an analogous blank sample for comparison.

The blank composition is essentially identical to the reagent composition, except that it does not contain the compound of formula (I). The blank composition may have the buffer composition to ensure the pH is identical to the reagent composition, although this is typically not used.

Most importantly, the blank composition contains the same solvent and (if present) approximately the same amounts of salt as the reagent composition. This ensures that the blank sample mixes and phase separates in the same way as the test sample.

By the "same solvent" is meant that any solvents present in the reagent composition are also present in the blank composition. Typically, the only solvent present in the reagent composition is water, although as noted above a phase transfer agent may be present. If a phase transfer agent is present in the reagent composition, this is also preferably present in the blank composition.

Of course, what is actually important is that the blank sample and test sample have similar compositions, differing only in the presence or absence of the compound of formula (I) and optionally the buffer. Whether the phase transfer agent is present in the blank composition, the reagent composition or diluent composition is therefore less relevant, providing that the compositions of the resultant blank and test samples are as close as possible.

Once the blank sample is obtained, the color chart can be viewed in combination with the blank sample to give a more representative color for the predetermined iron levels. This may be done by using a translucent color chart and aligning it in combination with the aqueous phase of the blank sample (either in front or behind), and viewing a white light source through the combination.

Alternatively, if spectroscopic means are being used, the blank sample can be subtracted from the test sample to provide the absorption spectrum of the iron complex.

Thus, the present invention relates to a method for determining the concentration of iron ions in a hydrocarbon composition, said method comprising:

a) providing a hydrocarbon composition;
b)
   i. reacting a first amount of the hydrocarbon composition with a reagent composition and optionally a diluent composition comprising a non-polar solvent to provide a test sample,
      characterized in that
      the reagent composition comprises water and a compound according to formula (I):

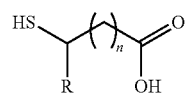

wherein
n denotes an integer from 0 to 3, and
R denotes H, alkyl or aryl, and
wherein the reagent composition has a pH of 7.5 or above; and
   ii. combining a second amount of the hydrocarbon composition with a blank composition comprising water and optionally a diluent composition comprising a non-polar solvent to provide a blank sample, wherein the blank composition does not contain a compound of formula (I),
   wherein the first amount and the second amounts are the same;
c) determining the concentration of iron ions in the hydrocarbon sample by determining the amount of complex formed between the compound of formula (I) and iron ions in the test sample, wherein the analysis comprises comparing the test sample and the blank sample.

By "comparing the test sample and the blank sample" is meant that the test sample is analysed by taking account of the blank sample in the analysis of the test sample. Typically, this is by subtracting the blank sample from the test sample, as may be done when doing the comparison using spectroscopic means. Alternatively, the blank sample could be combined with a reference color chart to provide a modified color chart for comparison with the test sample.

Preferably, the reagent composition corresponds to the blank composition, except it additionally includes the compounds of formula (I) and optionally a buffer.

A suitable apparatus for carrying out the invention is shown in FIG. 1. The apparatus comprises a housing (5), two cuvettes (3, 4) for holding the test and blank sample, and a color chart in the form of a rotatable disc (7) having a series of colored segments (8) and optionally a numerical concentration scale (not shown) around its perimeter (8). The apparatus has two openings where the cuvettes may be placed, with observation windows (1, 2) for each cuvette. The rotatable disc is placed in a slot (6) and is sized so that the graded colors (8) are in registration with the observation window (2) for viewing the blank sample (4). Typically, the rotatable disc (7) is translucent, and the blank sample (4) can be observed through the colored track (8). However, observing the colored track through the blank sample would work equally as well. The rotatable disc (7) can be rotated to until the color of the test sample (3) matches the blank sample (4) and graded color (8). Typically, the rotatable disc (7) also includes a scale (not shown), which is aligned with a result window (not shown) in the apparatus (5). When the colors match, the amount of iron complex can be read from the result window.

Such apparatus are known in the art, but nevertheless form part of the invention as an additional component in the kit of the invention.

The exact color chart to be used in the method of the invention will of course differ for each type of compound of formula (I), as well as the actual concentrations of iron ions which are being measured. However, it would be well within the remit of the skilled person to formulate a suitable color chart for any given range of iron concentrations and compound of formula (I). This can be done by preparing known concentrations of aqueous ferrous ions, and introducing excess amounts of the compound of formula (I) to ensure all of the ions form a complex. The observed color can then be used on the color chart for the respective iron concentrations.

Nevertheless, by way of guidance, the peak wavelength of the iron thioglycolate complex in water is 538 nm, and this complex has the color values at various concentrations are shown in Table 1 below:

TABLE 1

| ppm (by weight) | Color | | |
|---|---|---|---|
| | L* | a* | b* |
| 0 | 95 | 5 | 0 |
| 20 | 92 | 8 | −1 |
| 40 | 89 | 11 | −3 |
| 60 | 87 | 13 | −4 |
| 80 | 84 | 16 | −6 |
| 100 | 81 | 19 | −8 |
| 120 | 78 | 22 | −10 |
| 140 | 74 | 25 | −11 |
| 160 | 70 | 29 | −13 |
| 180 | 67 | 33 | −14 |
| 200 | 64 | 36 | −15 |
| 220 | 63 | 38 | −15 |
| 240 | 60 | 43 | −15 |
| 260 | 58 | 46 | −15 |
| 280 | 55 | 52 | −16 |
| 300 | 53 | 57 | −16 |
| 320 | 49 | 59 | −15 |
| 340 | 44 | 57 | −13 |
| 360 | 39 | 54 | −12 |
| 380 | 34 | 50 | −10 |
| 400 | 29 | 46 | −9 |

These color values are shown according to the CIE L*a*b* (CIELAB) color space. The various concentrations shown in the table are for iron concentrations in 0.2 ml of hydrocarbon sample when diluted into 5 ml water, in accordance with a preferred embodiment of the invention. Thus, 20 ppm iron in 0.2 ml of the hydrocarbon sample would provide 5 ml of water having CIELAB color values of 92, 8, −1.

Using this color chart, the method of the invention can reliably provide concentration ranges to an accuracy of around 20 ppm, although it is possible to distinguish compositions having concentrations of around 10 ppm in difference (e.g. 0 and 10 ppm).

The method of the invention has a great deal of flexibility. However, its advantage is its simplicity and the speed with which it can provide results. It is typically therefore carried out on a small scale in batch-wise tests. This allows periodic monitoring for the presence of ferrous and ferric ions in hydrocarbon compositions without the need for time consuming analytical techniques.

Preferred ranges for the various components in the blank and test sample are as shown in the table below (all values are % w/w):

| Test sample | General | Preferred | No Diluent | Diluent used |
|---|---|---|---|---|
| 1. Hydrocarbon Composition | 0.5-50% | 0.5-35% | 15-35% | 0.5-5% |
| 2. Non-Polar Solvent | 0-50% | 0-40% | 0% | 10-25% |
| 3. Transfer Reagent | 0-50% | 10-40% | 10-30% | 20-40% |
| Total of 1, 2 and 3 | 5-70% | 25-45% | 25-45% | 25-45% |
| Formula (I) | 0.1-5% | 0.5-3% | 0.5-3% | 0.5-3% |
| Salt | 0-25% | 5-15% | 5-15% | 5-15% |
| Buffer Components | 0-10% | 0.5-4% | 0.5-4% | 0.5-4% |
| Water | 25-90% | 40-50% | 40-50% | 40-50% |

In terms of the blank, reagent and diluent compositions, the typical make up will be as follows:

| Reagent Composition | General | Preferred | No Diluent | Diluent |
|---|---|---|---|---|
| Formula (I) | 0.2-10% | 1-3% | 1-3% | 1-3% |
| Salt | 0-49% | 10-28% | 10-28% | 10-30% |
| Buffer Components | 0-20% | 1-8% | 1-8% | 1-8% |
| Transfer reagent | 0-40% | 0-30% | 15-30% | 0% |
| Water | 50-99% | 60-88% | 55-73% | 60-88% |

| Diluent Composition | General | Preferred | Most preferred |
|---|---|---|---|
| Non-polar solvent | 1-99% | 20-50% | 20-40% |
| Transfer reagent | 0-80% | 40-75% | 50-75% |
| Water | 0-5% | 0-3% | 0-3% |

| Blank Composition | General | Preferred | No Diluent | Diluent |
|---|---|---|---|---|
| Salt | 0-49% | 10-30% | 10-28% | 10-30% |
| Buffer Components | 0-20% | 0-8% | 0-8% | 0-8% |
| Transfer reagent | 0-40% | 0-30% | 15-30% | 0% |
| Water | 50-99% | 60-88% | 55-75% | 60-90% |

Generally speaking, the method of the invention is carried out with small hydrocarbon samples, and manageable quantities of test and blank samples. In order to achieve the approximate water content of the test and blank samples shown in the table above, the method of the invention preferably uses the following amounts of reagent, blank, diluent and hydrocarbon compositions:

| Composition | General | Preferred | Most Preferred |
|---|---|---|---|
| Reagent/Blank* | 2-8 ml | 3-7 ml | 4-6 ml |
| Diluent | 2-8 ml | 3-7 ml | 4-6 ml |
| Hydrocarbon | 0.05-2 ml | 0.1-1 ml | 0.1-0.5 ml |

*the reagent and blank compositions should preferably be used in the same amounts.

It is generally preferred to include the transfer reagent in the diluent composition rather than the reagent composition, particularly when analysing highly viscous hydrocarbon compositions. This is because the method of the invention is generally easier to carry out by first mixing the diluent composition with the hydrocarbon composition, and then adding the reagent (or blank) composition to form the reagent (or blank) sample. The transfer reagent aids in the dissolution and thinning out of the hydrocarbon composition when present in the diluent composition.

Additionally, the presence of the salt may cause the transfer reagent to phase separate in the reagent and blank compositions. For this reason, it is preferred to use a diluent composition which can contain both the non-polar solvent and the transfer reagent. In such embodiments, the reagent, blank and diluent composition can all be homogeneous (i.e. single phase) mixtures, rendering them more suitable for use in the method of the invention.

In embodiments where a low viscosity hydrocarbon composition is being tested, the diluent composition may not be used, in which case the reagent (and blank) compositions preferably contain the transfer reagent, as shown in the tables above. However, this is less common in practice, as generally speaking the hydrocarbon sample itself has a higher economic value in comparison to the diluent composition. Therefore, generally speaking the diluent composition is preferably used. However, non-viscous hydrocarbon compositions may not need to be pre-mixed with the diluent composition, and the invention can easily be carried out by simply mixing the diluent and reagent (or blank) compositions at the same time.

For small hydrocarbon samples, it is preferable that the ratio of transfer reagent to non-polar solvent is from 10:1 to 1:5, more preferably from 5:1 to 1:2, more preferably from 4:1 to 1:1, such as e.g. about 2:1.

Step b) in the method of the invention may comprise:
Mixing the diluent composition and the hydrocarbon composition, preferably for a period of 5 seconds to 10 minutes, more preferably 10 seconds to 5 minutes, even more preferably 15 seconds to 2 minutes, then
Adding the reagent composition to form the test sample and mixing the resultant sample, preferably for a period of 5 seconds to 10 minutes, more preferably 10 seconds to 5 minutes, even more preferably 15 seconds to 2 minutes, then
Allowing the test sample to phase separate, preferably for a period of 1 minute to 10 minutes, more preferably for a period of 2 minutes to 5 minutes.

Alternatively, step b) in the method of the invention may comprise:
Mixing the reagent composition and the hydrocarbon composition to form the test sample, preferably for a period of 5 seconds to 10 minutes, more preferably 10 seconds to 5 minutes, even more preferably 15 seconds to 2 minutes, then
Allowing the test sample to phase separate, preferably for a period of 1 minute to 10 minutes, more preferably for a period of 2 minutes to 5 minutes.

Alternatively, step b) in the method of the invention may comprise:
Mixing the reagent composition, the diluent composition and the hydrocarbon composition to form the test sample, preferably for a period of 5 seconds to 10 minutes, more preferably 10 seconds to 5 minutes, even more preferably 15 seconds to 2 minutes, then
Allowing the test sample to phase separate, preferably for a period of 1 minute to 10 minutes, more preferably for a period of 2 minutes to 5 minutes.

Analogous steps are carried out for the formation of the blank sample, wherein instead of the reagent composition the blank composition is used.

Thus, the method of the invention preferably takes from 1 to 20 minutes, more preferably about 1 to 10 minutes, for example about 5 minutes in total. This is significantly faster than previously known methods of analysing hydrocarbon compositions for ferrous and ferric ions, and represents a very useful methodology to give semi-quantitative results without the need to use laborious analytical techniques.

The invention is further characterised by the following non limiting examples:

EXAMPLE 1

Diluent Composition
63.5% (w/w) Isopropyl alcohol
36.0% (w/w) Heavy distillate (CAS #64741-65-7)
0.5% (w/w) Deionised water
Reagent Composition
% (w/w) Sodium chloride
0.5% (w/w) Concentrated (36%) hydrochloric acid
1.5% (w/w) Monoethanolamine (99%)
2.0% (w/w) Thioglycolic acid (98%)
% (w/w) 0.88 s.g. Ammonia solution
75% (w/w) Deionised water
Blank Composition
22.0% (w/w) Sodium chloride
78.0% (w/w) Deionised water 5 ml of Diluent Composition is dispensed into each of two 10 ml color comparator cuvettes before 5 ml of Reagent Composition is added to one cuvette and 5 ml of Blank Composition is added to the other; finally, 0.2 ml of a used cylinder oil sample is added to each one.

Once capped, the cuvettes are shaken vigorously for 30 s and then left to stand for 270 s, by which point the liquid contents will have separated into two layers.

In the cuvette containing the Test sample, any iron (III) in the oil sample has been reduced to iron (II) by thioglycolic acid and extracted, along with any iron compounds that started in the +2 oxidation state, into the lower aqueous layer. The thioglycolic acid serves a dual purpose in this test because it forms a colored complex with the iron (II) in the aqueous layer.

In the cuvette containing Blank Sample, there is no thioglycolic acid for the iron compounds to form a complex with, so the only color in the lower aqueous layer is due to the dissolution of trace water-soluble compounds from within the oil sample.

After separation the Blank Sample and the Test sample cuvettes are inserted into the left and right-hand chambers of the comparator, respectively (see FIG. 1).

A color chart, calibrated using various concentrations of a suitable iron (II) compound (see Table 1 above), is then used to measure the concentration of iron in the sample.

Clearly there are a number of variations that could be made to this method including, but not limited to, the subtle alteration of the Diluent Composition, Reagent Composition, and Blank Composition or the adoption of a more sophisticated means of determining the concentration of iron in the aqueous layer, such as a colorimeter or a UV-visible absorption spectrometer.

Although the principles, embodiments and operation of the present invention have been described in detail herein, this is not to be construed as being limited to the particular illustrative forms disclosed. They will thus become apparent to those skilled in the art that various modifications of the embodiments herein can be made without departing from the spirit or scope of the invention.

The invention claimed is:

1. A method for determining the concentration of iron ions in a hydrocarbon composition, said method comprising:
   a) providing a hydrocarbon composition;
   b) reacting the hydrocarbon composition with a reagent composition and optionally a diluent composition comprising a non-polar solvent to provide a test sample, wherein the reagent composition comprises water and a compound according to formula (I):

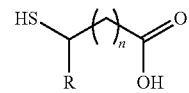

wherein
   n denotes an integer from 0 to 3, and
   R denotes H, alkyl or aryl, and
   wherein the reagent composition has a pH of 7.5 or above; and
   c) determining the concentration of iron ions in the hydrocarbon sample by determining the amount of complex formed between the compound of formula (I) and iron ions in the test sample.

2. The method of claim 1, wherein step b) comprises:
   i. reacting a first amount of the hydrocarbon composition with said reagent composition and optionally said diluent composition to provide a test sample, and
   ii. combining a second amount of the hydrocarbon composition with a blank composition comprising water and optionally said diluent composition to provide a blank sample, wherein the blank composition does not contain a compound of formula (I),
   wherein the first amount and the second amounts are the same;
   and wherein step c) comprises comparing the test sample and the blank sample.

3. The method according to claim 2, wherein step b) comprises:
   either:
      mixing the diluent composition and the hydrocarbon composition,
      adding the reagent composition to form the test sample and mixing the resultant sample, and
      allowing the test sample to phase separate to form an aqueous phase and a hydrocarbon phase;
   or:
      mixing the reagent composition, the diluent composition and the hydrocarbon composition to form the test sample, and
      allowing the test sample to phase separate to form an aqueous phase and a hydrocarbon phase;
   and wherein
      the blank sample is prepared in an analogous manner using the blank composition in place of the reagent composition.

4. The method of claim 3, wherein step c) comprises detecting the complexed iron ions in the aqueous phase of the test sample using colorimetry or UV-Vis spectroscopy, optionally by subtracting the blank sample.

5. The method of claim 3, wherein step c) comprises comparing a color of the aqueous phase of the test sample with a reference color chart, optionally viewed in combination with the aqueous phase of the blank sample.

6. The method of claim 2, wherein the reagent composition and the blank composition comprise a salt.

7. The method of claim 2, wherein the reagent composition and the blank composition comprises a buffer.

8. The method of claim 1, wherein the hydrocarbon composition is engine oil.

9. The method of claim 1, wherein, in the compound of formula (I):

n denotes 0; and

R denotes H or methyl.

10. The method of claim 1, wherein the diluent composition further comprises a phase transfer agent.

11. The method of claim 10, wherein the phase transfer agent is an alcohol.

12. The method of claim 11, wherein the phase transfer agent is isopropyl alcohol.

13. The method of claim 1, wherein the non-polar solvent is a petroleum distillate.

14. The method of claim 1, wherein the hydrocarbon composition is spent engine oil.

* * * * *